United States Patent [19]

Outlaw et al.

[11] Patent Number: 4,678,638

[45] Date of Patent: Jul. 7, 1987

[54] HIGHLY BRANCHED AMINO HEXAHYDROPYRIDINES

[75] Inventors: Benjamin T. Outlaw, Webster Groves; Bernardus A. Oude Alink, St. Louis, both of Mo.

[73] Assignee: Petrolite Corporation, St. Louis, Mo.

[21] Appl. No.: 856,267

[22] Filed: Apr. 28, 1986

Related U.S. Application Data

[63] Continuation-in-part of Ser. No. 758,196, Jul. 24, 1985, abandoned, which is a continuation-in-part of Ser. No. 239,075, Feb. 27, 1981, abandoned.

[51] Int. Cl.⁴ .................... C07D 211/58; C23F 11/06
[52] U.S. Cl. ..................................... 422/13; 546/184; 546/185; 546/223; 546/244; 252/390
[58] Field of Search ............... 546/184, 223, 244, 185; 252/390, 392; 422/13

[56] References Cited

U.S. PATENT DOCUMENTS 4,081,450  3/1978  Zimmerman ........................ 546/185

FOREIGN PATENT DOCUMENTS 233410  9/1958  Australia ............................ 546/185

OTHER PUBLICATIONS

Fieser & Fieser; Reagents for Organic Synthesis; vol. 3, (1972); pp. 9, 280–281.
Fieser & Fieser; Reagents for Organic Synthesis; vol. 4, (1974); pp. 7, 202.
The Merck Index of Chemicals and Drugs, (7th Ed.), 1960, p. 1446.
Noller; Chemistry of Organic Compounds, (3rd Ed.), 1965, pp. 582, 583, 668.

Primary Examiner—Joseph Paul Brust
Attorney, Agent, or Firm—S. B. Ring

[57] ABSTRACT

This invention relates to amino hexahydropyridines, and to the preparation and use thereof as corrosion inhibitors.

12 Claims, No Drawings

HIGHLY BRANCHED AMINO HEXAHYDROPYRIDINES

This application is a continuation-in-part of Ser. No. 758,196, now abandoned, filed July 24, 1985 which in turn is a continuation-in-part of Ser. No. 239,075, filed Feb. 27, 1981, now abandoned.

This invention relates to amino hexahydropyridines and to the preparation and use thereof.

In copending application Ser. No. 772,972, filed Sept. 5, 1985, there is described and claimed a method of reacting aldehydes and ammonia to afford cyclic diamines of the formula

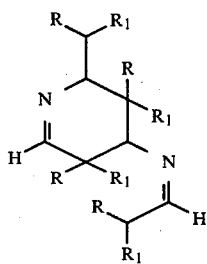

wherein R and $R_1$ are the same or different and independently represent alkyl or phenyl groups. Thus, R and $R_1$ may represent methyl, ethyl, propyl, isopropyl, butyl, isobutyl, amyl, hexyl, 2-ethylhexyl, 3-ethylhexyl, heptyl, octyl, nonyl, decyl, phenyl and alkylphenyl such as methylphenyl, ethylphenyl, propylphenyl, butylphenyl and the like. The method of Ser. No. 772,972 is carried out by the dimerization of a vinylimine I in presence of a Lewis acid catalyst at 160°–190° C. The route to the desired cyclic diamine may proceeds thru an intermediate via an intermolecular aldol type condensation to an imine II followed by an intramolecular aldol type condensation to the cyclic diamine III.

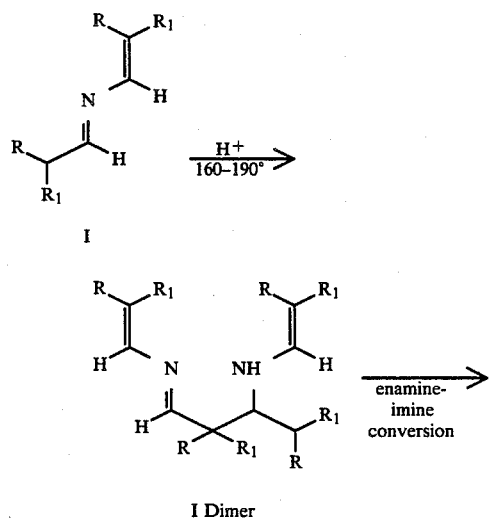

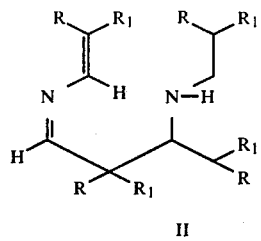

II

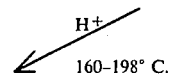

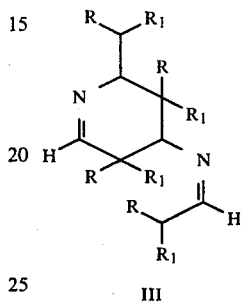

III

The cyclic diamine III consists of a mixture of stereoisomeric products. The acid catalyst may be any Lewis acid, for example, HCl, $NH_4Cl$, $NH_4NO_3$, $AlCl_3$, p-toluene sulfonic acid, etc.

The mixture of cyclic diamines III upon hydrolysis affords a mixture of aminopyridines IV.

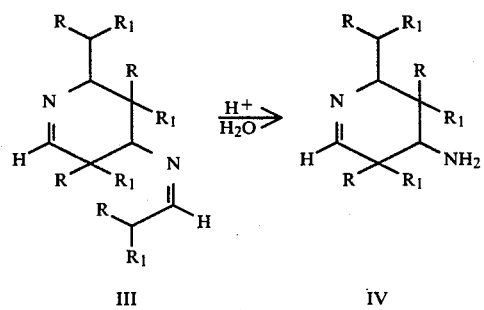

We have now discovered that the cyclic diamines can be reduced by any suitable method to amino hexahydropyridines.

One of the methods of reduction involves the treatment of either III or IV with a metal borohydride such as sodium borohydride.

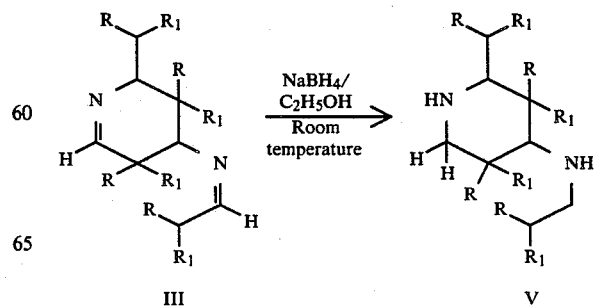

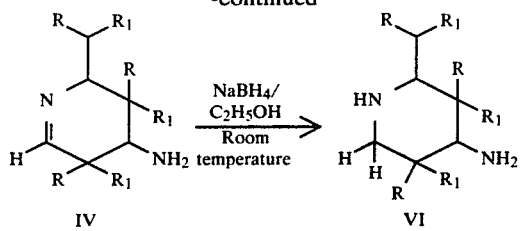
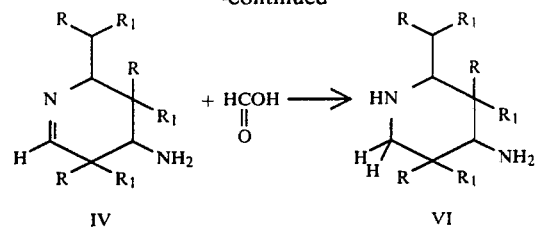

The Leuckart reduction of III which consists of treatment with a mixture of formaldehyde and formic acid yields a mixture of products VII and VIII. The major product being VIII.

The following examples are presented for purposes of illustration and not of limitation.

EXAMPLE 1

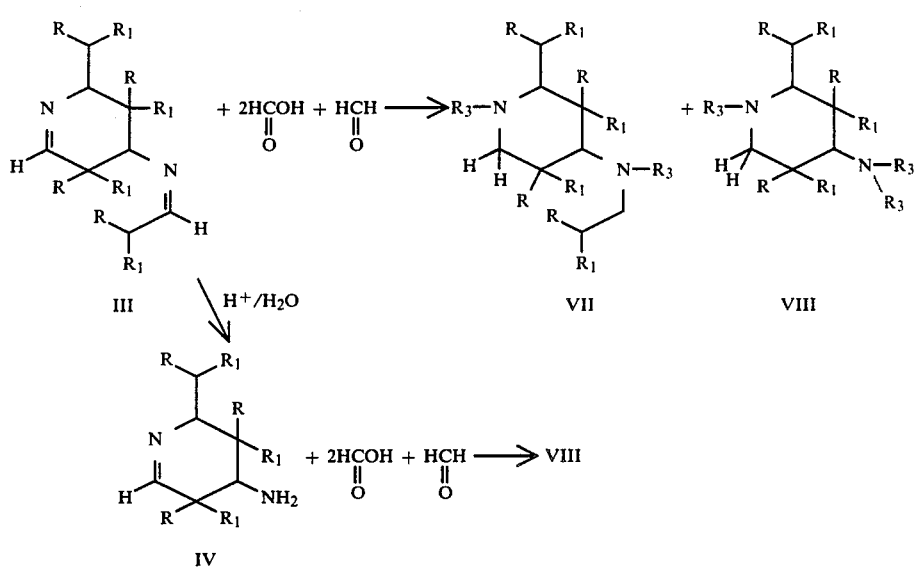

$R_3 = H$ or $CH_3$ or a combination of the two.

Compound VIII is the major product since the side chain is first cleared via said hydrolysis to IV followed by the reductive methylation.

Reduction of III with formic acid produces at the same time two products due to the hydrolysis reaction that occurs.

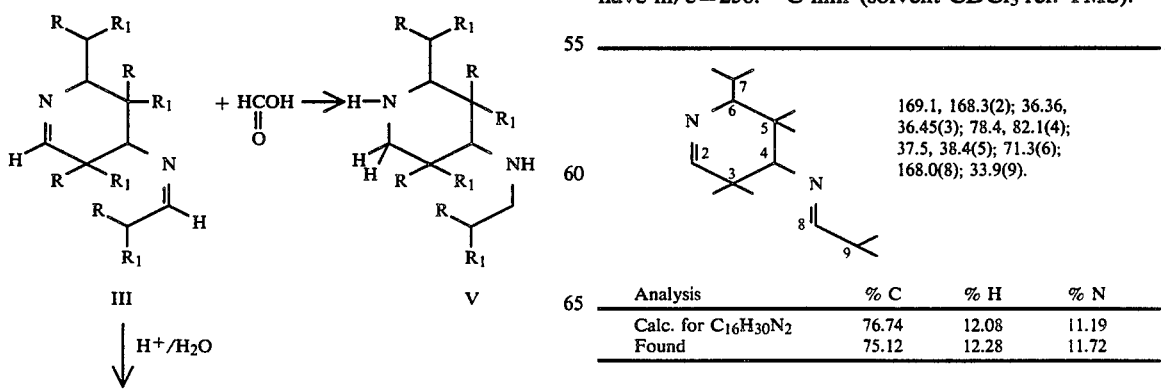

Dimerization of the vinylimine followed by Intramolecular Aldol type condensation to cyclic diamine 4-(3-Methyl-1-azabutenyl)-6-(1-methylethyl)-3,4,5,6-tetrahydro-3,3,5,5-tetramethyl pyridine (III $R=R_1=CH_3$)

A mixture of 100 g 2,6-dimethyl-4-azahepta-2,4-diene I and 1.2 g of p-toluene sulfonic acid was heated at 160° for 113 hrs. Ninety seven grams of the crude product was distilled under diminished pressure. The fraction $b_{0.03}79°-80°$ (44.3 g) was identified as III($R=R_1=CH_3$). Two products in GC (45:55), both have m/e=250. $^{13}C$ nmr (solvent $CDCl_3$ ref. TMS).

169.1, 168.3(2); 36.36, 36.45(3); 78.4, 82.1(4); 37.5, 38.4(5); 71.3(6); 168.0(8); 33.9(9).

| Analysis | % C | % H | % N |
|---|---|---|---|
| Calc. for $C_{16}H_{30}N_2$ | 76.74 | 12.08 | 11.19 |
| Found | 75.12 | 12.28 | 11.72 |

EXAMPLE 2

Hydrolysis to Another Diamine

4-Amino-6-(1-methylethyl)-3,4,5,6-tetrahydro-3,3,5,5-tetramethyl pyridine (III R=R$_1$=CH$_3$)

A mixture of 5 g of distilled III and 25 ml 5N HCl was refluxed for 25 hrs. The reaction mixture was extracted with ether. The acidic aqueous fraction was basified with 20% NaOH which was then extracted with ether. The ether extract was evaporated to yield 3.1 g of IV. Two products in GC/MS (45:55), both have m/e=196. $^{13}$C nmr (solvent CDCl$_3$, ref. TMS).

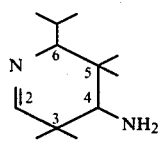

IV 168.2(2); 57.5, 63.14(4); 71.9, 73.6(6).

EXAMPLE 3

Sodium borohydride reduction of 4-(3-methyl-1-azabutenyl)-6-(1-methylethyl)-3,4,5,6-tetrahydro-3,3,5,5-tetramethyl pyridine III (R=R$_1$=CH$_3$) to Hexahydro-4-(3-methyl-1-azabutyl)-6-(1-methylethyl)-3,3,5,5-tetramethyl pyridine V A mixture of 5 g of distilled III and 0.85 g of sodium borohydride was stirred overnight at room temperature. The resulting product was extracted with ether. The ether extract was evaporated to dryness and acidified with 5N HCl. This acidic solution was extracted with ether and the aqueous layer was basified with 20% NaOH. The basic solution was extracted with ether and the ether extract was evaporated to yield 1.7 g of V. Two products in GC MS (45:55) both have m/e=254. $^{13}$C nmr (solvent CDCl$_3$ ref. TMS).

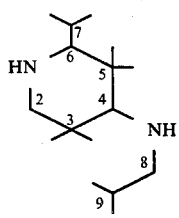

V 55.2, 60.4(2); 36.7, 37.1(3); 66.0, 71.7(4); 40.6, 41.7(5); 71.9, 73.2(6); 61.9(8).

EXAMPLE 4

Sodium borohydride reduction of 4-amino-6-(1-methylethyl)-3,4,5,6-tetrahydro-3,3,5,5-tetramethyl pyridine IV (R=R$_1$=CH$_3$) to 4-Amino-hexahydro-6-(1-methylethyl)-3,3,5,5-tetramethyl pyridine VI (R=R$_1$=CH$_3$)

A mixture of 1.5 g of IV and 0.5 g of sodium borohydride in 20 ml of ethanol was stirred overnight at room temperature. The reaction mixture was extracted with ether. The ether extract was evaporated to dryness and acidified with 5N HCl. The acidic solution was extracted with ether and the aqueous layer was basified with 20% NaOH. The basic aqueous layer was extracted with ether. The ether extract was evaporated to yield 0.3 g of VI. GC MS had two products (45:55) both of which m/e=198. $^{13}$C nmr (solvent CDCl$_3$, ref. TMS).

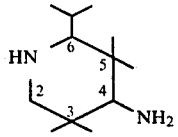

VI 54.5, 60.3(2); 34.9, 35.4(3); 64.7, 66.1(4); 38.7, 40.0(5); 65.1, 71.6(6).

EXAMPLE 5

Leuckart reduction of III to hexahydro-1-methyl-4-(3-methyl-1-azabutyl)-6-(1-methylethyl)-3,3,5,5-tetramethyl pyridine VII and 1-methyl-4-amino-hexahydro-6-(1-methylethyl)-3,3,5,5-tetramethylpyridine VIII (R=R$_1$=CH$_3$)

A mixture of 10 g of distilled III, 6.5 g of formaldehyde and 15 g of 90% formic acid were heated with stirring at reflux (83°-102°) for 24 hrs. The resulting mixture was acidified with 12.5 ml of 5N HCl. This acidic mixture was extracted with ether and the aqueous layer was made basic with 20% NaOH. The basic solution was extracted with ether and the ether layer was evaporated to yield 7.1 g of product. Two major products were found in GC MS having m/e=212 and m/e=282.

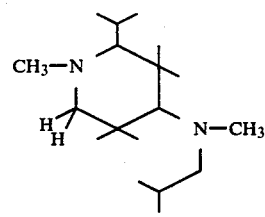

VII m/e = 282

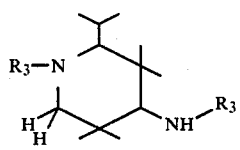

VIII

R$_3$ = H or CH$_3$ m/e = 212

EXAMPLE 6

Formic acid reduction of III to hexahydro-4-(3-methyl-1-azabutyl)-6-(1-methylethyl)-3,3,5,5-tetramethyl pyridine V and 4-amino-hexahydro-6-(1-methylethyl)-3,3,5,5-tetramethyl pyridine VI (R=R$_1$=CH$_3$).

A mixture of 10 g of III and 8.2 g of 90% formic acid was heated with stirring at reflux (115°-123°) for 18 hrs. The resulting mixture was then refluxed for 6 hrs. with 25 ml 5N HCl. This acidic mixture was extracted with ether and the aqueous layer was basified with 20% NaOH. The basic solution was extracted with ether and the ether layer was evaporated to dryness to yield 6.9 g of product. Two major products were found in GC MS having m/e=198 and m/3=254.

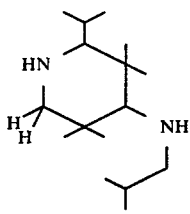

m/e = 254

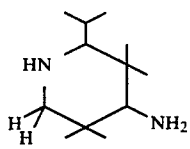

m/e = 198

EXAMPLE 7

This example illustrates the utility of the compounds of the invention as corrosion inhibitors in a standard laboratory $CO_2$ sparged brine coupon test.

The compounds of Examples 3 and 4 (100% active) were each added at a concentration of 1000 ppm (parts per million) to 12,000 TDS (Total Dissolved Solids) brine sparged (saturated) with $CO_2$.

The compound of Example 3 reduced general corrosion of standard AISI 1018 steel coupons by 90% over 12 hrs. as compared to the corrosion in uninhibited brine.

The compound of Example 4 reduced general corrosion of standard AISI 1018 steel coupons by 93% over 12 hrs. as compared to the corrosion in uninhibited brine.

It is contemplated that all of the novel compounds disclosed herein would exhibit similar corrosion inhibition properties.

We claim:
1. A compound of the formula

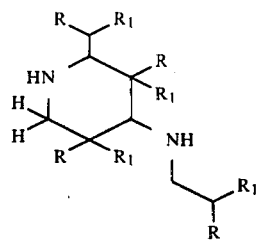

wherein R and R1 are the same or different and independently represent alkyl, phenyl or alkylphenyl.

2. Compound of claim 1 wherein R and $R_1$ represent alkyl.

3. Compound of claim 2 wherein said alkyl is methyl.

4. Compound of claim 1 wherein R and $R_1$ represent phenyl.

5. Compound of claim 1 wherein R represents alkyl and $R_1$ represents phenyl.

6. A compound of the formula

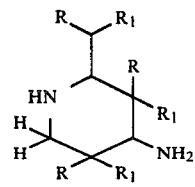

wherein R and $R_1$ are the same or different and independently represent alkyl, phenyl or alkylphenyl.

7. Compound of claim 6 wherein R and $R_1$ represent alkyl.

8. Compound of claim 7 wherein said alkyl is methyl.

9. Compound of claim 6 wherein R and $R_1$ represent phenyl.

10. Compound of claim 6 wherein R represents alkyl and $R_1$ represents phenyl.

11. Method of inhibiting corrosion of metal which comprises intimately contacting said metal with a corrosion inhibiting amount of a composition comprising a compound of claim 1.

12. Method of inhibiting corrosion of metal which comprises intimately contacting said metal with a corrosion inhibiting amount of a composition comprising a compound of claim 6.

* * * * *